United States Patent [19]

Chiang

[11] Patent Number: 5,420,028
[45] Date of Patent: May 30, 1995

[54] TRUNCATED HUMAN CHOLESTEROL 7α-HYDROXYLASE, METHOD OF PRODUCTION AND USE THEREOF

[75] Inventor: John Y. L. Chiang, Stow, Ohio

[73] Assignee: Northeastern Ohio Universities, Rootstown, Ohio

[21] Appl. No.: 135,510

[22] Filed: Oct. 13, 1993

[51] Int. Cl.$^6$ ............... C12N 9/02; C12N 15/72
[52] U.S. Cl. ................. 435/189; 435/252.33; 435/326.1
[58] Field of Search ............. 536/23.2; 435/252.33, 435/320.1, 69.1, 189

[56] References Cited

PUBLICATIONS

Karam, W. G. et al., "Polymorphisms of Human Cholesterol 7α-Hydroxylase", *Biochem. and Biophys. Res. Comm.* 185(2):588–595 (1992).
Breslow, J. L. et al., "Transgenic Mouse Models of Lipoprotein Metabolism and Atherosclerosis", *Proc. Natl. Acad. Sci. USA* 90: 8314–8318 (1993).
Cohen, J. C. et al., "Cloning of the Human Cholesterol 7α-Hydroxylase Gene (CYP7) and Localization to Chromosome 8q11–q12", *Genomics* 14: 153–161 (1992).
Nishimoto, M. et al., "Structure of the Gene Encoding Human Liver Cholesterol 7α-Hydroxylase", *Biochimica. et Biophysica. Acta.* 1172: 147–150 (1992).
Thompson, J. F. et al., "Cholesterol 7α-Hydroxylase Promoter Separated from Cyclophilin Pseudogene By Alu Sequence", *Biochimica et Biophysica Acta* 1168: 239–242 (1993).
Li, Y. C. et al., "The Expression of a Catalytically Active Cholesterol 7α-Hydroxylase Cytochrome P450 in *Escherichia coli*", *The Journal of Biological Chemistry* 266(29): 19186–19191 (1991).
Molowa, D. T. et al., "Transcriptional Regulation of the Human Cholesterol 7α-Hydroxylase Gene", *Biochemistry* 31: 2539–2544 (1992).
Nishimoto, M. et al., "Structural Analysis of the Gene Encoding Rat Cholesterol α-Hydroxylase, The Key Enzyme for Bile ...", *The Journal of Biological Chemistry* 266(10): 6467–6471 (1991).
Jelinek, D. F. et al., "Structure of the Rat Gene Encoding Cholesterol 7α-Hydroxylase", *Biochemistry* 29(34): 7781–7785 (1990).
Chiang, J. Y. L. et al., "Cloning and 5'-Flanking Sequence of a Rat Cholesterol 7α-Hydroxylase", *Biochimica et Biophysica Acta* 1132: 337–339 (1992).
Lusis, Aldons J., "The Mouse Model for Atherosclerosis", *TCM* 3(4): 135–143 (1993).
Dueland, Svein et al., "Effect of Dietary Cholesterol and Taurocholate on Cholesterol 7α-hydroxylase and Hepatic LDL Receptors in Inbred Mice", *Journal of Lipd Research* 34: 923–931 (1993).
Dueland, Svein et al., "Expression of 7α-Hydroxylase in Non-hepatic Cell Results in Liver Phenotypic Resistance of the Low Density Lipoprotein Receptor to Cholesterol Repression", *Journal of Biological Chemistry* 267(32): 22695–22698 (1992).
Noshiro et al. (1990) Febs Lett 268(1), 137–140; Abstract only.
Sambrook et al in "Molecular Cloning: A Laboratory Manual" 2nd Ed.; Cold Spring Harbor Laboratory Press, Cold Spring Harbor, 1989, 16.1–16.72 and 17.1–17.41.
Ramirez, M. I., et al, (1994) Mol. Cell. Biol. 14(4), 2809–2821.

*Primary Examiner*—Charles L. Patterson, Jr.
*Attorney, Agent, or Firm*—Foley & Lardner

[57] ABSTRACT

A catalytically active, truncated human cholesterol 7α-hydroxylase (CYP7) is provided. The truncated human CYP7 can be made recombinantly and thus recovered in relatively large amounts. Vectors and host cells for recombinant expression are provided, as well as an antibody which specifically recognizes an epitope of catalytically active, truncated human CYP7. Also provided is a method for screening a compound for its effect on expression of non-truncated human CYP7, and a method for screening a compound for its effect on non-truncated human CYP7 enzyme activity.

11 Claims, 4 Drawing Sheets

FIG. 1

```
   1 AGTTTAACTT TAGTAAGGAG TCTAGACCAT GGCCAGGAGA AGGCAAACGG GTGAACCACC
  61 TCTAGAGAAT GGATTAATTC CATACCTGGG CTGTGCTCTG CAATTTGGTG CCAATCCTCT
 121 TGAGTTCCTC AGAGCAAATC AAAGGAAACA TGGTCATGTT TTTACCTGCA AACTAATGGG
 181 AAAATATGTC CATTTCATCA CAAATCCCTT GTCATACCAT AAGGTGTTGT GCCACGGAAA
 241 ATATTTTGAT TGGAAAAAAT TTCACTTTGC TACTTCTGCG AAGGCATTTG GGCACAGAAG
 301 CATTGACCCG ATGGATGGAA ATACCACTGA AAACATAAAC GACACTTTCA TCAAAACCCT
 361 GCAGGGCCAT GCCTTGAATT CCCTCACGGA AAGCATGATG GAAAACCTCC AACGTATCAT
 421 GAGACCTCCA GTCTCCTCTA ACTCAAAGAC CGCTGCCTGG GTGACAGAAG GGATGTATTC
 481 TTTCTGCTAC CGAGTGATGT TTGAAGCTGG GTATTTAACT ATCTTTGGCA GAGATCTTAC
 541 AAGGCGGGAC ACACAGAAAG CACATATTCT AAACAATCTT GACAACTTCA AGCAATTCGA
 601 CAAAGTCTTT CCAGCCCTGG TAGCAGGCCT CCCCATTCAC ATGTTCAGGA CTGCGCACAA
 661 TGCCCGGGAG AAACTGGCAG AGAGCTTGAG GCACGAGAAC CTCCAAAAGA GGGAAAGCAT
 721 CTCAGAACTG ATCAGCCTGC GCATGTTTCT CAATGACACT TTGTCCACCT TTGATGATCT
 781 GGAGAAGGCC AAGACACACC TCGTGGTCCT CTGGGCATCG CAAGCAAACA CCATTCCAGC
 841 GACTTTCTGG AGTTTATTTC AAATGATTAG GAACCCAGAA GCAATGAAAG CAGCTACTGA
 901 AGAAGTGAAA AGAACATTAG AGAATGCTGG TCAAAAAGTC AGCTTGGAAG GCAATCCTAT
 961 TTGTTTGAGT CAAGCAGAAC TGAATGACCT GCCAGTATTA GATAGTATAA TCAAGGAATC
1021 GCTGAGGCTT TCCAGTGCCT CCCTCAACAT CCGGACAGCT AAGGAGGATT TCACTTTGCA
1081 CCTTGAGGAC GGTTCCTACA ACATCCGAAA AGATGACATC ATAGCTCTTT ACCCACAGTT
1141 AATGCACTTA GATCCAGAAA TCTACCCAGA CCCTTTGACT TTTAAATATG ATAGGTATCT
1201 TGATGAAAAC GGGAAGACAA AGACTACCTT CTATTGTAAT GGACTCAAGT TAAAGTATTA
1261 CTACATGCCC TTTGGATCGG GAGCTACAAT ATGTCCTGGA AGATTGTTCG CTATCCACGA
1321 AATCAAGCAA TTTTTGATTC TGATGCTTTC TTATTTTGAA TTGGAGCTTA TAGAGGGCCA
1381 AGCTAAATGT CCACCTTTGG ACCAGTCCCG GCAGGCTTG GGCATTTTGC CGCCATTGAA
1441 TGATATTGAA TTTAAATATA AATTCAAGCA TTTGTGAATA CATGGCTGGA ATAAGAGGAC
1501 ACTAGATGAT ATTACGGCCA TGGC 3'
```

FIG. 4

MOLECULAR-WEIGHT 55281  #LENGTH 483

```
  1 M A R R R Q T G E P P L E N G L I P Y L G C A L Q F G A N P
 31 L E F L R A N Q R K H G H V F T C K L M G K Y V H F I T N P
 61 L S Y H K V L C H G K Y F D W K K F H F A T S A K A F G H R
 91 S I D P M D G N T T E N I N D T F I K T L Q G H A L N S L T
121 E S M M E N L Q R I M R P P V S S N S K T A A W V T E G M Y
151 S F C Y R V M F E A G Y L T I F G R D L T R R D T Q K A H I
181 L N N L D N F K Q F D K V F P A L V A G L P I H M F R T A H
211 N A R E K L A E S L R H E N L Q K R E S I S E L I S L R M F
241 L N D T L S T F D D L E K A K T H L V V L W A S Q A N T I P
271 A T F W S L F Q M I R N P E A M K A A T E E V K R T L E N A
301 G Q K V S L E G N P I C L S Q A E L N D L P V L D S I I K E
331 S L R L S S A S L N I R T A K E D F T L H L E D G S Y N I R
361 K D D I I A L Y P Q L M H L D P E I Y P D P L T F K Y D R Y
391 L D E N G K T K T T F Y C N G L K L K Y Y M P F G S G A T
421 I C P G R L F A I H E I K Q F L I L M L S Y F E L E L I E G
451 Q A K C P P L D Q S R A G L G I L P P L N D I E F K Y K F K
481 H L *
```

5,420,028

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCCATGGCCA GGAGAAGGCA AACGGGT        27

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:2:

```
Met Ala Arg Arg Arg Glu
 1               5
```

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | |
|---|---:|
| GCCATGGCCG TAATATCATC TAG | 23 |

( 2 ) INFORMATION FOR SEQ ID NO:4:

( i ) SEQUENCE CHARACTERISTICS:
        ( A ) LENGTH: 1524 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

| | |
|---|---:|
| AGTTTAACTT TAGTAAGGAG TCTAGACCAT GGCCAGGAGA AGGCAAACGG GTGAACCACC | 60 |
| TCTAGAGAAT GGATTAATTC CATACCTGGG CTGTGCTCTG CAATTTGGTG CCAATCCTCT | 120 |
| TGAGTTCCTC AGAGCAAATC AAAGGAAACA TGGTCATGTT TTTACCTGCA AACTAATGGG | 180 |
| AAAATATGTC CATTTCATCA CAAATCCCTT GTCATACCAT AAGGTGTTGT GCCACGGAAA | 240 |
| ATATTTTGAT TGGAAAAAAT TTCACTTTGC TACTTCTGCG AAGGCATTTG GCACAGAAG | 300 |
| CATTGACCCG ATGGATGGAA ATACCACTGA AAACATAAAC GACACTTTCA TCAAAACCCT | 360 |
| GCAGGGCCAT GCCTTGAATT CCCTCACGGA AAGCATGATG GAAAACCTCC AACGTATCAT | 420 |
| GAGACCTCCA GTCTCCTCTA ACTCAAAGAC CGCTGCCTGG GTGACAGAAG GATGTATTC | 480 |
| TTTCTGCTAC CGAGTGATGT TTGAAGCTGG GTATTTAACT ATCTTTGGCA GAGATCTTAC | 540 |
| AAGGCGGGAC ACACAGAAAG CACATATTCT AAACAATCTT GACAACTTCA AGCAATTCGA | 600 |
| CAAAGTCTTT CCAGCCCTGG TAGCAGGCCT CCCCATTCAC ATGTTCAGGA CTGCGCACAA | 660 |
| TGCCCGGGAG AAACTGGCAG AGAGCTTGAG GCACGAGAAC CTCCAAAAGA GGGAAAGCAT | 720 |
| CTCAGAACTG ATCAGCCTGC GCATGTTTCT CAATGACACT TTGTCCACCT TTGATGATCT | 780 |
| GGAGAAGGCC AAGACACACC TCGTGGTCCT CTGGGCATCG CAAGCAAACA CCATTCCAGC | 840 |
| GACTTTCTGG AGTTTATTTC AAATGATTAG GAACCCAGAA GCAATGAAAG CAGCTACTGA | 900 |
| AGAAGTGAAA AGAACATTAG AGAATGCTGG TCAAAAAGTC AGCTTGGAAG GCAATCCTAT | 960 |
| TTGTTTGAGT CAAGCAGAAC TGAATGACCT GCCAGTATTA GATAGTATAA TCAAGGAATC | 1020 |
| GCTGAGGCTT TCCAGTGCCT CCCTCAACAT CCGGACAGCT AAGGAGGATT TCACTTTGCA | 1080 |
| CCTTGAGGAC GGTTCCTACA ACATCCGAAA AGATGACATC ATAGCTCTTT ACCCACAGTT | 1140 |
| AATGCACTTA GATCCAGAAA TCTACCCAGA CCCTTTGACT TTTAAATATG ATAGGTATCT | 1200 |
| TGATGAAAAC GGGAAGACAA AGACTACCTT CTATTGTAAT GGACTCAAGT TAAAGTATTA | 1260 |
| CTACATGCCC TTTGGATCGG GAGCTACAAT ATGTCCTGGA AGATTGTTCG CTATCCACGA | 1320 |
| AATCAAGCAA TTTTTGATTC TGATGCTTTC TTATTTTGAA TTGGAGCTTA TAGAGGGCCA | 1380 |
| AGCTAAATGT CCACCTTTGG ACCAGTCCCG GGCAGGCTTG GGCATTTTGC CGCCATTGAA | 1440 |
| TGATATTGAA TTTAAATATA AATTCAAGCA TTTGTGAATA CATGGCTGGA ATAAGAGGAC | 1500 |
| ACTAGATGAT ATTACGGCCA TGGC | 1524 |

( 2 ) INFORMATION FOR SEQ ID NO:5:

( i ) SEQUENCE CHARACTERISTICS:
        ( A ) LENGTH: 482 amino acids
        ( B ) TYPE: amino acid
        ( D ) TOPOLOGY: linear ( x i ) SEQUENCE DESCRIPTION: SEQ ID NO:5:

```
Met Ala Arg Arg Arg Gln Thr Gly Glu Pro Pro Leu Glu Asn Gly Leu
 1               5                  10                  15

Ile Pro Tyr Leu Gly Cys Ala Leu Gln Phe Gly Ala Asn Pro Leu Glu
            20                  25                  30

Phe Leu Arg Ala Asn Gln Arg Lys His Gly His Val Phe Thr Cys Lys
        35                  40                  45

Leu Met Gly Lys Tyr Val His Phe Ile Thr Asn Pro Leu Ser Tyr His
    50                  55                  60

Lys Val Leu Cys His Gly Lys Tyr Phe Asp Trp Lys Lys Phe His Phe
65                  70                  75                  80

Ala Thr Ser Ala Lys Ala Phe Gly His Arg Ser Ile Asp Pro Met Asp
                85                  90                  95

Gly Asn Thr Thr Glu Asn Ile Asn Asp Thr Phe Ile Lys Thr Leu Gln
            100                 105                 110

Gly His Ala Leu Asn Ser Leu Thr Glu Ser Met Met Glu Asn Leu Gln
        115                 120                 125

Arg Ile Met Arg Pro Pro Val Ser Ser Asn Ser Lys Thr Ala Ala Trp
    130                 135                 140

Val Thr Glu Gly Met Tyr Ser Phe Cys Tyr Arg Val Met Phe Glu Ala
145                 150                 155                 160

Gly Tyr Leu Thr Ile Phe Gly Arg Asp Leu Thr Arg Arg Asp Thr Gln
                165                 170                 175

Lys Ala His Ile Leu Asn Asn Leu Asp Asn Phe Lys Gln Phe Asp Lys
            180                 185                 190

Val Phe Pro Ala Leu Val Ala Gly Leu Pro Ile His Met Phe Arg Thr
        195                 200                 205

Ala His Asn Ala Arg Glu Lys Leu Ala Glu Ser Leu Arg His Glu Asn
    210                 215                 220

Leu Gln Lys Arg Glu Ser Ile Ser Glu Leu Ile Ser Leu Arg Met Phe
225                 230                 235                 240

Leu Asn Asp Thr Leu Ser Thr Phe Asp Asp Leu Glu Lys Ala Lys Thr
                245                 250                 255

His Leu Val Val Leu Trp Ala Ser Gln Ala Asn Thr Ile Pro Ala Thr
            260                 265                 270

Phe Trp Ser Leu Phe Gln Met Ile Arg Asn Pro Glu Ala Met Lys Ala
        275                 280                 285

Ala Thr Glu Glu Val Lys Arg Thr Leu Glu Asn Ala Gly Gln Lys Val
    290                 295                 300

Ser Leu Glu Gly Asn Pro Ile Cys Leu Ser Gln Ala Glu Leu Asn Asp
305                 310                 315                 320

Leu Pro Val Leu Asp Ser Ile Ile Lys Glu Ser Leu Arg Leu Ser Ser
                325                 330                 335

Ala Ser Leu Asn Ile Arg Thr Ala Lys Glu Asp Phe Thr Leu His Leu
            340                 345                 350

Glu Asp Gly Ser Tyr Asn Ile Arg Lys Asp Asp Ile Ile Ala Leu Tyr
        355                 360                 365

Pro Gln Leu Met His Leu Asp Pro Glu Ile Tyr Pro Asp Pro Leu Thr
    370                 375                 380
```

| | | | | | | | | | | | | | | |
|---|---|---|---|---|---|---|---|---|---|---|---|---|---|---|
| Phe 385 | Lys | Tyr | Asp | Arg | Tyr 390 | Leu | Asp | Glu | Asn | Gly 395 | Lys | Thr | Lys | Thr 400 |
| Phe | Tyr | Cys | Asn | Gly 405 | Leu | Lys | Leu | Lys | Tyr 410 | Tyr | Met | Pro | Phe 415 | Gly |
| Ser | Gly | Ala | Thr 420 | Ile | Cys | Pro | Gly | Arg 425 | Leu | Phe | Ala | Ile | His 430 | Glu | Ile |
| Lys | Gln | Phe 435 | Leu | Ile | Leu | Met | Leu 440 | Ser | Tyr | Phe | Glu | Leu 445 | Glu | Leu | Ile |
| Glu | Gly 450 | Gln | Ala | Lys | Cys 455 | Pro | Pro | Leu | Asp | Gln | Ser 460 | Arg | Ala | Gly | Leu |
| Gly 465 | Ile | Leu | Pro | Pro | Leu 470 | Asn | Asp | Ile | Glu | Phe 475 | Lys | Tyr | Lys | Phe | Lys 480 |
| His | Leu | | | | | | | | | | | | | | |

TRUNCATED HUMAN CHOLESTEROL 7α-HYDROXYLASE, METHOD OF PRODUCTION AND USE THEREOF

Work related to subject matter described in this application was provided by research supported in part by NIH Grant GM 31584.

CROSS REFERENCE TO RELATED APPLICATIONS

U.S. patent application Ser. No. 08/135/488 "GENOMIC DNA OF HUMAN CHOLESTEROL 7α-HYDROXYLASE AND METHODS FOR USING IT" to Chiang, J.; and U.S. patent application Ser. No. 08/135,511 "CHOLESTEROL 7α-HYDROXYLASE GENE REGULATORY ELEMENTS AND METHODS FOR USING THEM" to Chiang, J. are both filed concurrently herewith and their disclosures are expressly incorporated herein by reference in their entirety.

BACKGROUND OF THE INVENTION

High serum cholesterol is commonly associated with an increased risk of heart attack, atherosclerosis and circulatory disorders. In addition, a variety of diseases are caused by cholesterol catabolism disorders, such as gallstone disease, atherosclerosis, hyperlipidemia and some lipid storage diseases.

The major pathway for disposal of cholesterol in the body is by secretion of cholesterol and bile acids into the gut. Bile contains free cholesterol and bile acids. The enzyme, cholesterol 7α-hydroxylase (CYP7) commits cholesterol to bile acid synthesis and catalyzes the first and rate-limiting step of bile acid synthesis in the liver. Specifically, CYP7 catalyzes, in the presence of reductase and a reducing agent such as NADPH, the initial hydroxylation of cholesterol at the 7α-position, thereby forming 7α-hydroxycholesterol. Thus, by increasing synthesis of bile acids, this enzyme plays a key role in the liver by depleting hepatic cholesterol pools, resulting in increased low density lipoprotein (LDL) uptake and a lowering of serum cholesterol levels.

Bile acids are physiological agents which are important in the solubilization of lipid-soluble vitamins, sterol and xenobiotics. Bile acids are synthesized exclusively in the liver and are secreted to the intestines where they are modified to secondary bile acids. Most bile acids are reabsorbed in the ileum and recirculated to the hepatocytes via the portal vein.

The feedback of bile into the liver is known to inhibit cholesterol 7α-hydroxylase and thus inhibit the overall rate of bile acid synthesis. Cholesterol 7α-hydroxylase, therefore, has been a subject of active investigations to elucidate the regulatory mechanisms of bile acid synthesis in the liver.

It is known that an interruption of bile acid reabsorption, such as that caused by the bile sequestrant, cholestyramine, or by a bile fistula, stimulates the rate of bile acid synthesis and cholesterol 7α-hydroxylase activity in the liver. Recent achievements in the purification and cloning of cholesterol 7α-hydroxylase cDNA have advanced knowledge about the regulation of this enzyme at the molecular level. It has become clear that cholesterol 7α-hydroxylase activity in the liver is regulated primarily at the gene transcriptional level by bile acids, cholesterol, hormones, diurnal rhythm and other factors. However, the molecular mechanism underlying the regulation of cholesterol 7α-hydroxylase gene expression remains undetermined.

To understand the structure and function of human CYP7 and its regulation by factors, such as bile acids, cholesterol and hormones, it is essential to purify the human CYP7 enzyme. However, the CYP7 enzyme is present in an extremely low levels in human liver; therefore, it has not been possible to isolate sufficient quantities of purified, functional enzyme from human livers.

Although a cDNA molecule encoding human CYP7 enzyme has been determined, recombinant expression of human CYP7 has not heretofore been achieved. Karam and Chiang, Biochem. Biophys. Res. Commun. 185: 588 (1992). Recently, a strategy to express a catalytically active, truncated rat cholesterol 7α-hydroxylase in E. coli was disclosed. Li and Chiang, J. Biol. Chem. 266 (29): 19186 (1991). The disclosures of both of those publications are expressly incorporated herein by reference. In the latter publication, it was disclosed that the expression of a membrane-bound hydrophobic protein in E. coli is difficult because the bacteria lacks internal membranes. Via PCR, a modified cDNA was generated that encoded a truncated enzyme lacking the N-terminal 23 amino acid residues of the rat cholesterol 7α-hydroxylase enzyme. The resulting protein was expressed, predominantly in the cytosol of the bacteria. The purified recombinant enzyme was active, as determined by its ability to hydroxylate cholesterol in a reconstituted system, and has a $K_m$ for cholesterol and $V_{max}$ similar to those of the rat microsomal (non-truncated) enzyme.

Despite the high sequence identity between the rat and human cholesterol 7α-hydroxylase, however, it previously has not been possible to express the human cholesterol 7α-hydroxylase in E. coli following the same strategy and using the same expression vector (pKK233-2) as that previously used for the expression of rat cholesterol 7α-hydroxylase. Thus, a catalytically active, recombinant human CYP7 enzyme is desirable. Recombinantly-expressed, truncated human CYP7 could be used to detect agents that stimulate or inhibit human CYP7's catalytic activity. Further, such recombinant protein can be used to produce anti-CYP7 antibodies which would be useful for screening assays, for example, to detect stimulated or inhibited production of human CYP7 in response to exposure of a compound to a human CYP7-producing culture.

SUMMARY OF THE INVENTION

An embodiment of the invention provides catalytically active, truncated human cholesterol 7α-hydroxylase (CYP7). Advantageously, the truncated human CYP7, which can be produced recombinantly and in relatively large recoverable amounts, has a specific activity that is at least a substantial fraction of the specific activity of truncated rat enzyme produced in accordance with Li and Chiang, J. Biol. Chem. 266 (29):19186 (199).

Another embodiment of this invention provides a catalytically active, truncated human CYP7, which lacks a membrane anchor region that is present in human CYP7. Advantageously, amino acids 1 to 24 of the membrane anchor region are deleted.

Other embodiments provide analogs of the catalytically active, truncated human CYP7 proteins of this invention.

Another embodiment comprises a fusion protein comprising catalytically active, truncated human CYP7, or a portion thereof, and a structural protein in addition to the truncated human CYP7. Advantageously, the structural protein is capable of ready expression in a particular host system such that production of truncated human CYP7 can be increased by virtue of the increased production of the structural protein.

Other embodiments provide DNA encoding the foregoing catalytically active, truncated human CYP7 proteins.

Other embodiments of the invention provide an expression vector and a host cell useful for recombinant expression of catalytically active, truncated human CYP7.

Yet other embodiments provide a method for producing catalytically active, truncated human CYP7, comprising the step of culturing a host cell according to this invention under conditions which permit production of catalytically active truncated human CYP7.

Another embodiment provides an antibody which specifically recognizes an epitope of catalytically active, truncated human CYP7.

Another embodiment provides a method for screening a compound for its effect on expression of non-truncated human CYP7. The method comprises the steps of (a) providing a host cell according to the invention under conditions which permit production of catalytically active truncated human CYP7, (b) contacting the host cell with a compound and (c) detecting the amount of catalytically active, truncated human CYP7 expressed by the host cell.

Another embodiment provides a method for screening a compound for its effect on non-truncated human CYP7 enzyme activity. The method comprises the steps of (a) contacting catalytically active, truncated human CYP7 with a compound and (b) measuring the catalytic activity of the catalytically active, truncated human CYP7.

Other embodiments and advantages of the invention will be set forth in part in the description that follows, and in part will be obvious from the description, or may be learned by practice of the invention.

BRIEF DESCRIPTION OF THE DRAWINGS

FIG. 1 provides the cDNA sequence (SEQ ID NO:4) of human CYP7. The ATG start codon is located at positions 29-31 and the TGA stop codon at positions 1475-1477.

FIG. 4 provides the truncated human CYP7 amino acid sequence. (SEQ ID NO:5).

DETAILED DESCRIPTION OF THE PREFERRED EMBODIMENTS

Figure 2:
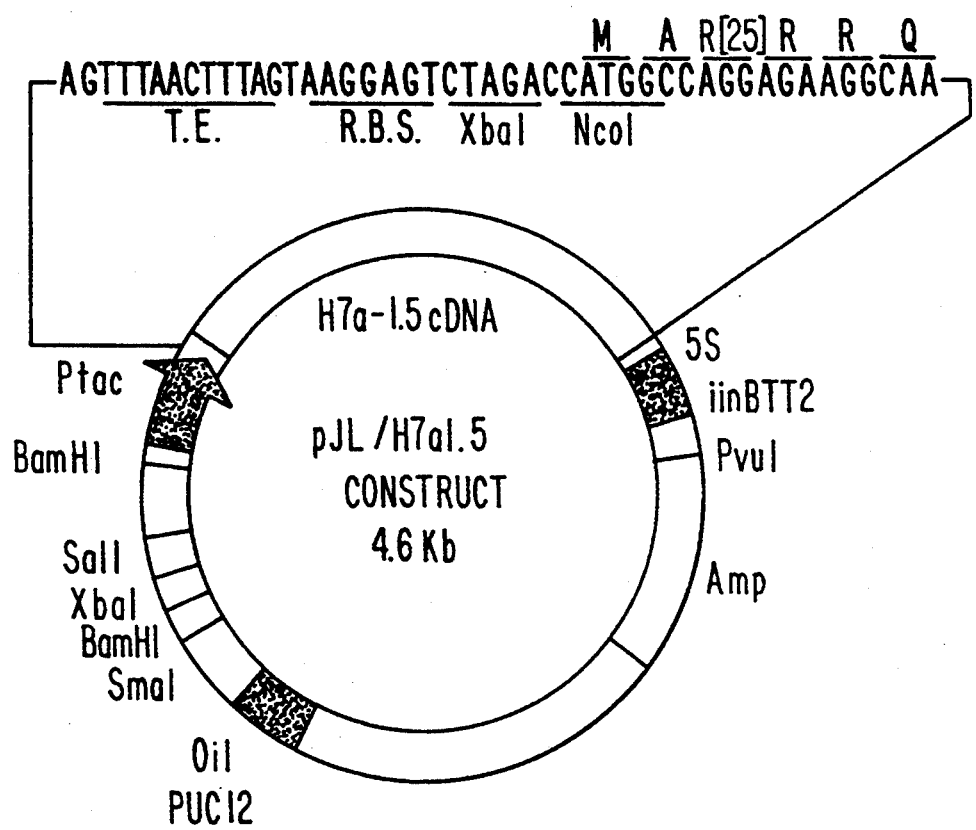
FIG. 2 illustrates a recombinant expression vector construct for truncated human cholesterol 7α-hydroxylase cDNA. The PCR-generated cDNA, H7α1.5, was inserted in an NcoI digested expression vector pJL, as described in Example 1. Abbreviations are as follows: Transcription enhancer (T.E.), ribosome binding site (R.B.S.), Xba I and NcoI (restriction enzyme sites), M (methionine), A (alanine), R[25] (arginine, residue 25 of full-length protein); G (glutamine). In the vector, restriction enzyme sites, the ampicillin resistance gene (Amp), the origin of replication of PUC12 (Ori PUC12) and the tac promoter (ptac) are indicated. Nucleotides 1–46 SEQ ID NO:4 are also shown in this Figure.

Surprisingly, it has been discovered that, by using a bacterial strain having the characteristics of the E. coli strain TOPP3, and a vector having the characteristics of the expression vector pJL, catalytically active, truncated human CYP7 now can be expressed recombinantly. No other bacteria strains or expression vectors have been found that possess the characteristics permitting expression of the truncated human CYP7 enzyme. In particular, "E. Coli TOPP3-pJL/H7α1.5" contains the expression vector pJL/H7α1.5 DNA and encodes a truncated human CYP7 cDNA that is expressed in relatively large amounts in the bacterial cytosol.

Therefore, one embodiment of the present invention is a catalytically active, truncated human CYP7 protein. "Truncated" as used herein means that a portion, all or substantially all of the complete membrane anchor region of human CYP7 has been deleted. Advantageously, all or a substantial portion of amino acids 1 to 24, which comprise the membrane anchor region in human CYP7, are deleted. FIG. 4 provides the amino acid sequence of a catalytically active, truncated human CYP7 protein in accordance with this invention.

By "catalytically active" it is meant that the CYP7 protein is capable of catalyzing, in the presence of reductase and a reducing agent such as NADPH, the initial hydroxylation of cholesterol at the 7α-position, thereby forming 7α-hydroxycholesterol. Catalytic activity can be measures in known assays using several well known parameters such as $K_M$ and $V_{Max}$. Advantageously, catalytic activity can be measured as specific activity and compared with the specific activity of the catalytically active, truncated rat CYP7 discussed above. Most advantageously, specific activity of the truncated human CYP7 and the truncated rat CYP7 are measured in simultaneously run assays under identical conditions. Otherwise, assay-to-assay variations in activity may be observed by virtue of differences in the assay conditions.

Also encompassed by the invention is an analog of catalytically active, truncated human CYP7. In accordance with this invention, the term "analog" includes a protein having conservative amino acids substitutions or deletions that do not eliminate the enzymatic activity of the truncated human CYP7. Advantageously, the analog retains a specific activity that is at least about ten percent (10%) of the specific activity of truncated rat CYP7 produced in accordance with Li and Chiang, J. Biol. Chem. 266: 19186 (1991).

Skilled artisans will readily appreciate that an analog of catalytically active, truncated human CYP7 having the amino acid sequence in FIG. 4 (SEQ ID NO:5) readily can be constructed. The analog can be the prepared, for example, by exploiting the degeneracy in the genetic code, or by effecting a point mutation which yields an amino acid substitutions and/or additions or deletions of non-essential amino acids. Advantageously, the amino acid substitutions can be conservative in accordance with well known principles.

By way of example, an analog advantageously includes those proteins having at least about 85%, and more advantageously at least about 90% amino acid sequence homology, which proteins still possesses substantially similar enzymatic activity as that of the truncated rat CYP7. Advantageously, the catalytically active, truncated human CYP7 or analog thereof will possess at least about 10%, advantageously at least about 25%, more advantageously at least about 50%, more advantageously at least about 75%, and more advantageously at least about 90% of the specific activity of catalytically active, truncated rat CYP7 as measured in simultaneous assays run under identical conditions.

The present invention further includes a fusion protein comprising catalytically active, truncated human CYP7, or a portion thereof, and a structural protein in addition to the truncated human CYP7. Advantageously, the structural protein is capable of ready expression in a particular host system. Advantageously, the structural protein is a protein which is produced in relatively high quantity by the host. In this way, production of truncated human CYP7 can be increased by virtue of the increased production of the structural protein. Thus a vector is provided that in addition to a truncated hCYP7 gene, such as H7α1.5, further contains a gene encoding at least one additional structural protein. The additional protein is advantageously selected from among proteins that are expressed at high levels in *E. coli*, including factor IX, for example. See Nagai et al., *Meth. Enzym.* 153: 461 (1987), the contents of which are hereby expressly incorporated by reference.

Additional embodiments of this invention comprise DNAs which encode the proteins described herein. Those skilled in the art will appreciate that many different DNAs can encode a single protein, and preferred codons routinely can be employed for different expression systems. All such DNAs are contemplated within this invention. Further, within this embodiment are DNA sequences that hybridize under stringent conditions, preferably under highly stringent conditions, with the DNA sequence encoding catalytically active, truncated human CYP7. According to the present invention the term "stringent conditions" means hybridization conditions comprising a salt concentration of 4× SSC (NaCl-citrate buffer) at 62°–66° C., and "high stringent conditions" means hybridization conditions comprising a salt concentration of 0.1× SSC at 68° C.

Yet another embodiment of the invention provides a method of making catalytically active, truncated human CYP7 protein recombinantly. One method comprises culturing a host cell containing the gene encoding the protein or an analog thereof, advantageously *E. coli* TOPP3 (ATCC 69401), under conditions which permit production of the protein. Advantageously, the method further comprises the step of recovering quantities of protein. Advantageously, as discussed below, high quantities of the polypeptide are obtained. Skilled artisans will appreciate the various ways in which recombinant proteins of this invention can be prepared.

Compared to a corresponding amount of rat CYP7 produced according to Li and Chiang, *J. Biol. Chem.* 266: 19186 (1991), the level of truncated human CYP7 expressed according to the invention is increased substantially, i.e., by a four-fold increase in yield. According to the present invention, a method is provided for obtaining expression of at least 30 nmol human cholesterol 7α-hydroxylase in one liter of *E. coli* culture, but more advantageously, 50 nmol/liter. This markedly improved yield can be achieved by subcloning the cDNA in a pJL expression vector to form pJL/R7α1.5 which can then be transformed into *E. coli* strain TOPP3. The pJL expression vector is characterized by possessing (i) a transcription enhancer sequence, located upstream from and proximal to a ribosomal binding site, and (ii) an origin of replication for pUC12.

Another embodiment of this invention is an expression vector containing the DNA encoding truncated CYP7, especially an expression vector additionally containing a transcription enhancer region (T.E.), particularly wherein said T.E. is located upstream from and proximal to a ribosomal binding region. Preferably, the vector also has an origin of replication for pUC12 as well, or some other origin known to be associated with the expression of high copy numbers of an inserted gene. Typically, the T.E. and the ribosomal binding region are operably attached to the truncated CYP7 cDNA. An advantageous embodiment of the present invention includes the expression vector pJL/H7α1.5 containing DNA encoding truncated CYP7 and the transfected *E. coli* TOPP3 (ATCC 69401) as a host cell.

Also included is a method of making a truncated CYP7 protein that employs an expression vector containing a transcription enhancer region (T.E.), particularly wherein said T.E. is located upstream from and proximal to a ribosomal binding region and which preferably has an origin of replication for pUC12. This method can be exploited to make truncated CYP7 proteins having a species origin other than human or rat. Thus, for example, hamster, murine and other species of truncated CYP7 made by using an expression vector (without the human gene insert) and an *E. coli* TOPP3 host cell are encompassed by the invention. In particular, according to the present invention, *E. coli* TOPP3 transfected with a pJL expression vector containing a CYP7 genomic insert of the desired species of CYP7 is used to produce another species of truncated CYP7.

*E. coli* TOPP3-pJL/H7α1.5 was deposited on Aug. 25, 1993, at the American Type Culture Collection, ATCC, 12301 Parklawn Drive, Rockville, Md. 20852, U.S.A. under the accession number ATCC 69401.

Also included in the present invention are monoclonal and polyclonal antibodies, or binding fragments thereof, specific for truncated human CYP7, i.e., which specifically recognize an epitope of catalytically active, truncated human CYP7. Methods for the preparation of such antibodies are also contemplated (see Example 4 below). Further, an anti-truncated CYP7 antibody can be used in a method to screen compounds for their ability to inhibit or stimulate CYP7 enzyme expression (see Example 4). For example, either an antibody according to the invention or an antibody against non-truncated human CYP7 is used to detect the expression of truncated human CYP7 in an assay. Thus, to screen for an agent that enhances CYP7, an agent can be added to a culture of TOPP3-pJL/H7α1.5 for a period of time sufficient for the agent to modulate expression, after which expressed truncated human CYP7 is detected using any of the above-described antibodies in a Western blot. An increase in protein content, relative to the level of control enzyme expression from cells not exposed to the agent, detects an agent that stimulates expression of human CYP7. Results of such as assay optionally are confirmed with an in vivo transgenic animal assay, such as that described in U.S. application Ser. No. 08/135,488 filed Oct. 13, 1993.

Truncated CYP7 obtained according to the present invention also can be used in a screening assay as an indicator of non-truncated CYP7 activity. A compound can be screened to determine whether it increases or decreases either the level of enzyme expression or its activity. A compound can be tested either alone or in the presence of physiological agents or drugs (see Examples 3 and 4). Information obtained can be used to screen for potentially beneficial drugs, and particularly for the design of drugs capable of treating patients with defects in bile acid synthesis and cholesterol metabolism.

A compound screening method according to the present invention can be performed as follows. To assess a compound's effect on CYP7 enzyme activity in human liver, the compound, in varying dosages, is tested in the enzyme assay method. Such a method, is advantageously performed on truncated CYP7, purified from *E. coli* TOPP3-pJL/H7α1.5. A method for detecting the enzyme's activity is described in Example 3 herein. A compound's effect on CYP7 enzyme levels is determined, for example, using a CYP7 specific antibody in a Western blot assay, as described in Example 4.

The following examples merely illustrate the invention and, as such, are not to be considered as limiting the invention set forth in the claims.

EXAMPLE 1

PRODUCTION AND EXPRESSION OF TRUNCATED HUMAN CHOLESTEROL 7α-HYDROXYLASE IN *E. COLI*

Two primers were designed for the generation of a truncated human cholesterol 7α-hydroxylase cDNA by polymerase chain reaction using the full length human clone PHC7F as the template. Karam and Chiang, *Biochem. Biophys. Res. Commun.* 185: 588–95 (1992). The 5'-primer had a sequence of 5'-GCCATGGCCAG-GAGAAGGCAAACGGGT-3 (SEQ ID NO:1), which encoded an N-terminus with a sequence of Met-Ala-Arg(25)-Arg(26)-Arg(27)-Glu(28) (SEQ ID NO:2), etc. The 3'-primer had a sequence of GCCATGGCC-GTAATATCATCTAG-3'(SEQ ID NO:3), which was complementary to the cDNA sequence from 1599 to 1612 near the 3'-end of the coding region. The cDNA generated was sequenced to confirm the human sequence (FIG. 1) (SEQ ID NO:4). This cDNA was ligated to the Nco I site (GCCATG) of the pJL plasmid. The recombinant construct, pJL/H7α1.5 (FIG. 2), was then transformed into a battery of bacteria strains.

It was found that the TOPP3 strain of *E. coli* harboring pJL/H7α1.5 was capable of expressing truncated human cholesterol 7α-hydroxylase in very high amounts. Bacteria carrying pJL/H7α1.5 were cultured in "Terrific" broth containing 100 μg/ml ampicillin for 6 hours. One (1) mM IPTG was added to induce the production of protein at 30° C. for 15 to 18 hours. Addition of 2 mM δ-aminolevulinic acid in the culture increased the expression level by 100%. About 20 nmol of human cholesterol 7α-hydroxylase were expressed per liter of culture.

EXAMPLE 2

PURIFICATION OF THE BACTERIALLY EXPRESSED HUMAN CHOLESTEROL 7α-HYDROXYLASES

Culturing the bacteria carrying the recombinant vector encoding truncated human CYP7 was performed by inoculating 8 liters of Terrific broth containing 100 μg/ml ampicillin with a 6-hour culture of TOPP3-pJL/H7α1.5. This culture was grown at 37° C. until the O.D.$_{600}$ reached from about 0.4 to about 0.6, which occurred in about 3 hours. IPTG was added to a final concentration of 1 mM and incubation was carried out at 30° C. for 15 to 18 hours.

After induction, the cultures were harvested by centrifugation at 5,000 rpm for ten minutes at 4° C. The cells were then resuspended in 1/100 volume of buffer A (100 mM potassium phosphate, pH 7.4, 0.5% sodium cholate, 20% glycerol, 0.1 mM EDTA, 0.1 mM DTT and 0.5 mM PMSF). The cells were then lysed in buffer A with 200 μg/ml lysozyme. The supernatant was collected after spinning down the total lysate at 100,000× g for one (1) hour at 4° C. The pellet was resuspended thoroughly in the same buffer and centrifuged again. Both supernatants were combined and stored on ice overnight after the addition of 100 units of DNaseI. The clear lysate was then applied to an Octylamino Sepharose 4B column (2.6×15 cm). This column was washed and eluted with the same buffer. The eluted fractions were dialyzed against buffer B (10 mM potassium phosphate, pH 7.4, 0.2% sodium cholate, 0.2% Emulgen 911, 0.1 mMEDTA, 0.05 mMDTT, 0.5 mM phenyl methyl sufonyl fluoride (PMSF)), applied to a hydroxyapatite column (2.4×7 cm) and equilibrated with the same buffer. This column was then washed with 200 ml of 10 mM potassium phosphate buffer, then with 150 ml of 50 mM potassium phosphate buffer and then eluted with 300 ml of 100 mM potassium phosphate buffer. These three buffers also contained 20% glycerol, 0.3% sodium cholate, 0.05 mM EDTA, 0.1 mM DTT and 0.5 mM PMSF. The purified sample was brought to 0.2% Emulgen 911 and then dialyzed against 10 mM potassium phosphate buffer, pH 7.4, 20% glycerol, 0.1 mM EDTA, 0.1 mM DTT, 0.5 mM PMSF and 0.2% Emulgen 911 (buffer C). The sample was then applied to a second hydroxylapatite column (0.5×3.0 cm) equilibrated with buffer C and eluted with buffer C but containing 360 mM potassium phosphate. At this stage, the purity of the human cholesterol 7α-hydroxylase was confirmed by SDS-polyacrylamide gel electrophoresis.

EXAMPLE 3

CHARACTERIZATION OF THE PURIFIED HUMAN CHOLESTEROL 7α-HYDROXYLASE

The truncated enzyme was purified from recombinant bacteria. Purification methodology is described by Li and Chiang, *J. Biol. Chem.* 266 (29): 19186 (1991), the contents of which are expressly incorporated by reference herein in its entirety. The activity of CYP7, in both the presence and absence of the compound, is measured as described by Chiang, *Meth. Enzym.* 206: 483 (1991), the contents of which is expressly incorporated by reference herein in its entirety.

Purified truncated enzyme was active in the reconstitution of cholesterol 7α-hydroxylase activity in the presence of NADPH-cytochrome P450 reductase and phospholipid (purified CYP7 enzyme (0.1 nmoles), 2 units of NADPH-cytochrome P450 reductase, 40 μg/ml of L-dilauroyl-glyceryl-3-phosphorylcholine, 100 μM cholesterol in 10 μl of 45% Molecusol, 0.015% CHAPS (3-(3-cholamidopropyl) dimethylamino)-1-propanesulfonate), 0.1M potassium phosphate, pH 7.4, 1 mM EDTA, 5 mM DTT and 0.1% Emulgen 911). The addition of Molecusol, at varying concentrations, stimulated activity by three-fold. The reaction was started by the addition of 1 mM NADPH and proceeded for 20 minutes, at 37° C. Reactions were terminated by adding 0.8% sodium cholate. Products were oxidized by adding 1 unit of cholesterol oxidase and incubated at 37° C. for 10 minutes. The reaction mixture was extracted three (3) times with 6 ml each of petroleum ether and combined extracts were dissolved in 100 μl of acetonitrile:methanol (70:30; v/v) and analyzed on a C18 reverse-phase HPLC column as described previously. Chiang, *Meth. in Enzymol.* 206: 483–91 (1991).

Figure 3:
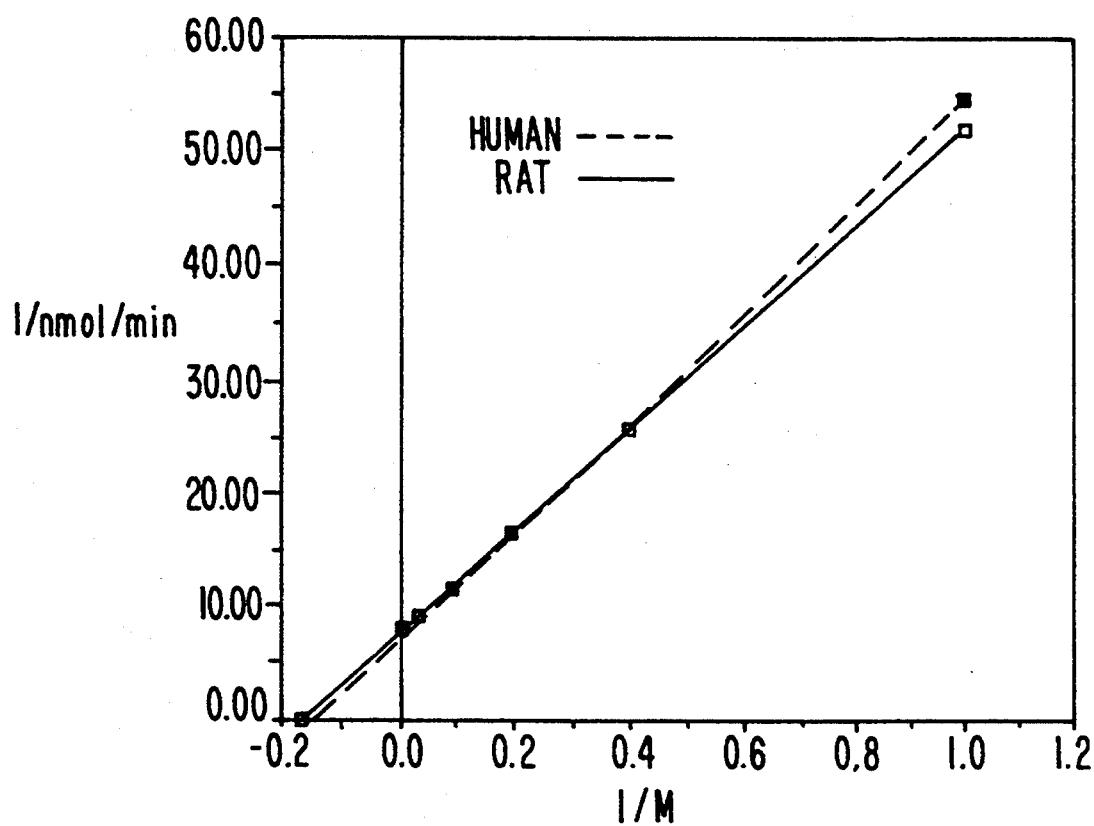
FIG. 3 illustrates a Lineweaver-Burke plot of activities of truncated human and truncated rat cholesterol 7α-hydroxylase in E. coli. Truncated CYP7 activity was measured using a reconstitution assay, such as that described in Example 3, at different concentrations of cholesterol, as indicated. Linear regression was used to draw the line.

The $K_m$ and $V_{max}$ for cholesterol have been determined in comparison with the truncated, bacterially expressed rat CYP7 enzyme (FIG. 3). The $K_m$ for the truncated human enzyme was 5.85 μM and $V_{max}$ was 0.13 nmol/min, which were similar to those of the truncated, bacterially expressed rat enzyme and of intact enzyme isolated from rat liver microsomes. Thus, the isolated truncated human CYP7 enzyme has similar kinetic properties to the truncated rat CYP7 enzyme.

EXAMPLE 4

ASSAY FOR SCREENING COMPOUNDS FOR ABILITY TO INHIBIT OR STIMULATE NON-TRUNCATED CYP7 ENZYME ACTIVITY IN HUMAN LIVER

A. Preparation of Antibodies Against the Purified Human Cholesterol 7α-Hydroxylase As mentioned above, an assay system using antibodies raised against purified, truncated human CYP7 is used to screen compounds for their ability to inhibit or stimulate non-truncated CYP7 enzyme activity in human liver. Antibodies to truncated human CYP7 can be produced as follows.

One (1) mg purified truncated CYP7 enzyme was mixed with an equal volume of Freund's adjuvant and 5 mg/ml of heat-killed microbacteria. The emulsified antigen mixtures were injected on the back of New Zealand white rabbits by intradermal injections on multiple sites. After six (6) weeks, 0.5 mg of purified human enzyme was mixed with incomplete adjuvant and used for booster injections to the same rabbits. Six (6) weeks later, blood samples were collected from ear veins and tested for the presence of antibodies by Ouchterlony double diffusion and by immunoblotting as described previously by Chiang et al., *J. Biol. Chem.* 265: 3889–97 (1990), incorporated by reference in its entirety.

For a Western Blot analysis, one (1) μg of purified human CYP7 enzyme was loaded on a 7.5% SDS-polyacrylamide gel, separated polypeptides were electrophoretically transferred to an Immobilon P membrane by a modified procedure reported previously. Chiang et al., supra. (1990). Diluted antisera were reacted with membrane and subsequently reacted with second antibody, anti-rabbit IgG conjugated with alkaline phosphatase, and then stained with nitroblue tetrazolium (NBT) and 5-bromo-4-chloro-3-indolylphosphate (DCIP) as described previously.

B. Assay Using Antibodies Against the Purified Human Cholesterol 7α-Hydroxylase

The specific antibody described above can be used in a screen assay to measure the inhibitory or stimulatory effects of a particular compound on the expression of CYP7 in human liver by a corresponding analysis of the effect on truncated CYP7. To quantitate the amount of expressed truncated enzyme in Western Blot analysis, such as described immediately above, varying concentrations of purified truncated human CYP7 enzyme, from 1 to 10 μgs, are run on adjacent lanes on the 7.5% SDS-polyacrylamide gel to those lanes containing the human CYP7 enzyme from the experimentally treated cells. A stimulation of truncated CYP7 expression is detected by a darker band, relative to control, on the Western blot. If a compound stimulates CYP7 enzyme expression and/or activity, then such an agent or drug could potentially be used to reduce cholesterol in humans. If an agent or drug inhibits CYP7 enzyme expression and/or activity, then such a compound should be used with caution because it potentially could increase serum cholesterol levels in humans.

It will be apparent to those skilled in the art that various modifications and variations can be made to the compositions of matter and processes of this invention. In particular, various kinds of screening assays are encompassed that employ truncated human CYP7 or its analogs. Thus, it is intended that the present invention covers the modifications and variations provided they fall within the scope of the appended claims and their equivalents.

---

What is claimed is:

1. An expression vector comprising DNA encoding truncated human CYP7, wherein said expression vector when transfected into *E. coli* TOPP3, expresses catalytically active, truncated human CYP7.

2. An expression vector according to claim 1, further comprising a transcription enhancer sequence, located upstream from and proximal to a ribosomal binding site, and an origin of replication for pUC12.

3. A host cell *E. coli* TOPP3, transfected with an expression vector according to claim 1, such that said host cell is capable of expressing catalytically active, truncated human CYP7.

4. A host cell according to claim 3, wherein said expression vector further comprises a transcription enhancer sequence located upstream from and proximal to a ribosomal binding site, and an origin of replication for pUC12.

5. A host cell according to claim 4, wherein said expression vector is pJL/H7α1.5.

6. A method for producing catalytically active, truncated human CYP7, comprising the step of culturing a host cell according to claim 3 under conditions which permit production of catalytically active truncated human CYP7.

7. A method for producing catalytically active, truncated human CYP7, comprising the step of culturing a host cell according to claim 4 under conditions which permit production of catalytically active truncated human CYP7.

8. A method according to claim 6, further comprising the step of purifying the truncated human CYP7 to obtain purified truncated human CYP7.

9. A method according to claim 8, further comprising the step of analyzing the quantity of the purified truncated human CYP7.

10. A method according to claim 9, wherein said analyzing is performed by Western blot assay employing an antibody that binds CYP7 specifically.

11. A host cell having the characteristics of ATCC 69401.

* * * * *